United States Patent [19]
Tsien et al.

[11] Patent Number: 5,955,453
[45] Date of Patent: Sep. 21, 1999

[54] MEMBRANE-PERMEANT PHOSPHOINOSITIDES

[75] Inventors: Roger Y. Tsien, La Jolla; Tao Jiang, San Diego, both of Calif.

[73] Assignee: The Regents of the University of California, Oakland, Calif.

[21] Appl. No.: 09/066,037

[22] Filed: Apr. 24, 1998

[51] Int. Cl.$^6$ ............... A61K 31/66; C07F 9/10; C07F 9/117; C07F 9/177; C07F 9/24

[52] U.S. Cl. ............ 514/103; 514/100; 514/118; 514/120; 514/121; 514/129; 549/220; 558/157; 558/160; 558/161; 558/179; 558/180; 558/185; 558/186

[58] Field of Search ............... 514/103; 558/160

[56] References Cited

U.S. PATENT DOCUMENTS 5,866,548  2/1999  Tsien et al. ............... 514/23

*Primary Examiner*—Michael G. Ambrose
*Attorney, Agent, or Firm*—Fish & Richardson P.C.

[57] ABSTRACT

Membrane-permeant phosphoinositides, including phosphatidylinositol phosphate esters, are described. A membrane-permeant phosphoinositide includes groups that neutralize the charges of the phosphate moieties of the phosphoinositide. A cell can be treated with the membrane-permeant phosphoinositide, which is then absorbed into the cell. The neutralizing groups can be removed intracellularly to afford the charged phosphoinositide.

39 Claims, 4 Drawing Sheets

MEMBRANE-PERMEANT PHOSPHOINOSITIDES

STATEMENT AS TO FEDERALLY SPONSORED RESEARCH

This invention was made with Government support under Grant (or Contract) No. NS27177, awarded by the National Institutes of Health. The Government has certain rights in this invention.

BACKGROUND OF THE INVENTION

A family of phosphoinositide 3-OH kinases (PI3K) biosynthesize D-3 phosphorylated inositol lipids. See, for example, Toker, A. and Cantley, L. C. Nature 387:673–676 (1997). These enzymes phosphorylate phosphatidylinositol, phosphatidylinositol-4- phosphate and phosphatidylinositol-4,5-bisphosphate on the D-3 position of the inositol ring to generate phosphatidylinositol-3-phosphate (PI(3)P), phosphatidylinositol-3,4-bisphosphate (PI(3,4)$P_2$) and phosphatidylinositol-3,4,5-trisphosphate (PIP$_3$), respectively. Some forms of PI3K, such as that of yeast Vps34p and its homologues, produce exclusively PI(3)P. In mammalian cells, PI(3)P is usually constitutively present.

PI(3,4)$P_2$ and PIP$_3$ are normally undetectable in unstimulated cells, but their concentrations can become transiently elevated within seconds to minutes following stimulation with various growth factors or cytokines. This behavior can be indicative of signaling roles for both PI(3,4)$P_2$ and PIP$_3$. Various PI3Ks can be activated through both tyrosine kinase and G-protein dependent pathways. Multiple putative downstream targets have been identified including $Ca^{2+}$-independent protein kinase C (PKC) isoforms δ, ε, ζ, and η, and proteins with pleckstrin homology domains such as Akt/PKB, as well as other proteins such as synaptotagamin.

SUMMARY OF THE INVENTION

In general, the invention features membrane-permeant phosphoinositides, including phosphatidylinositol phosphate esters. A membrane-permeant phosphoinositide includes groups that neutralize the charges of the phosphate moieties of the phosphatidylinositol. A cell can be treated with the membrane-permeant phosphoinositide, which is then absorbed into the cell. The neutralizing groups can be removed intracellularly to afford the charged phosphoinositide.

In one aspect, the invention features a membrane-permeant phosphoinositide. The membrane-permeant phosphoinositide can be a compound of formula:

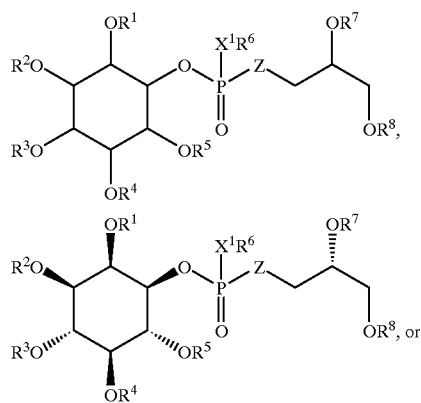

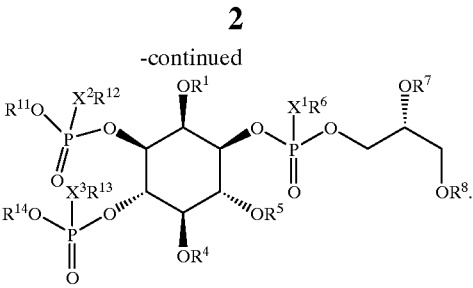

In the compound, $R^1$ is H, —$CH_2OC(O)CH_3$, —$CH_2OC(O)CH_2CH_3$, —$CH_2OC(O)$ $(CH_2)_2CH_3$, or a caging group, $R^2$ is H, —$CH_2OC(O)CH_3$, —$CH_2OC(O)CH_2CH_3$, —$CH_2OC(O)$ $(CH_2)_2CH_3$, or —$P(O)$ $(OR^{11})$ $(X^2R^{12})$, or a caging group, $R^3$ is H, —$CH_2OC(O)CH_3$, —$CH_2OC(O)CH_2CH_3$, —$CH_2OC(O)$ $(CH_2)_2CH_3$, —$P(O)$ $(OR^{13})$ $(X^3R^{14})$, or a caging group, $R^4$ is H, —$CH_2OC(O)CH_3$, —$CH_2OC(O)CH_2CH_3$, —$CH_2OC(O)$ $(CH_2)_2CH_3$, —$P(O)$ $(OR^{15})$ $(X^4R^{16})$, or a caging group, $R^5$ is H, —$CH_2OC(O)CH_3$, —$CH_2OC(O)CH_2CH_3$, —$CH_2OC(O)$ $(CH_2)_2CH_3$, or a caging group, each of $X^1$, $X^2$, $X^3$, and $X^4$, is, independently, S or O, each of $R^6$, $R^{11}$, $R^{12}$, $R^{13}$, $R^{14}$, $R^{15}$, and $R^{16}$ is, independently, H, —$CH_2OC(O)CH_3$, —$CH_2OC(O)CH_2CH_3$, or —$CH_2OC(O)$ $(CH_2)_2CH_3$, each of $R^7$ and $R^8$ is, independently, a saturated or unsaturated $C_4$–$C_{22}$ group;

Z is O, $CH_2$, or NH, and at least one of $R^6$, $R^{11}$, $R^{12}$, $R^{13}$, $R^{14}$, $R^{15}$, and $R^{16}$ is —$CH_2OC(O)CH_3$, —$CH_2OC(O)CH_2CH_3$, or —$CH_2OC(O)$ $(CH_2)_2CH_3$.

At least one of $R^2$, $R^3$, and $R^4$ can be a phosphorus-containing group. For example, $R^2$ can be —$P(O)$ $(OR^{11})$ $(X^2R^{12})$, $R^3$ can be —$P(O)$ $(OR^{13})$ $(X^3R^{14})$, or $R^4$ can be —$P(O)$ $(OR^{15})$ $(X^4R^{16})$. In preferred embodiments, at least two of $R^2$, $R^3$, and $R^4$ are phosphorus-containing groups. $R^2$ can be —$P(O)(OR^{11})$ $(X^2R^{12})$ and $R^3$ can be —$P(O)(OR^{13})$ $(X^3R^{14})$, $R^2$ can be —$P(O)$ $(OR^{11})$ $(X^2R^{12})$ and $R^4$ can be —$P(O)$ $(OR^{15})$ $(X^4R^{16})$, or $R^3$ can be —$P(O)$ $(OR^{13})$ $(X^3R^{14})$ and $R^4$ can be —$P(O)$ $(OR^{15})$ $(X^4R^{16})$. In other preferred embodiments, $R^2$, $R^3$, and $R^4$ are phosphorus-containing groups. In other embodiments, $R^2$ is —(O) $(OR^{11})$ $(X^2R^{12})$, $R^3$ is —$P(O)$ $(OR^{13})$ $(X^3R^{14})$, and $R^4$ is —$P(O)$ $(OR^{15})$ $(X^4R^{16})$.

In preferred embodiments, Z is O, each of $X^1$, $X^2$, $X^3$, and $X^4$ is O, or each of $R^6$, $R^{11}$, $R^{12}$, $R^{13}$, $R^{14}$, $R^{15}$, and $R^{16}$ is —$CH_2OC(O)CH_3$.

Each of $R^7$ and $R^8$ can be a saturated or unsaturated $C_4$–$C_{22}$ acyl, a $C_4$–$C_{22}$ alkyl, a $C_4$–$C_{22}$ alkenyl, or a $C_4$–$C_{22}$ polyene. For example, each of $R^7$ and $R^8$ can be derived from a fatty acid. A saturated or unsaturated $C_4$–$C_{22}$ acyl is a carbonyl-terminated alkyl, alkenyl, or polyene containing a total of 4–22 carbon atoms. The acyl, alkyl, alkenyl, or polyene can be branched or linear and can include cyclic groups. The acyl, alkyl, alkenyl, or polyene can be substituted with one or more hydroxy, amino, or halogen groups. The alkyl group is saturated and the alkenyl and polyene groups are unsaturated. The double bond of the alkenyl and the polyene can be positioned anywhere along the $C_4$–$C_{22}$ chain. The polyene group contains two or more double bonds (e.g., two to six double bonds) which can be conjugated or non-conjugated. Each of the double bonds of the polyene or alkenyl groups, independently, can be in a cis or trans configuration.

In preferred embodiments, each of $R^7$ and $R^8$ is, independently, —C(O) $(CH_2)_m CH_3$ where m is a integer between 4–20, inclusive, —C(O)—$(CH_2)_7 CH=CH(CH_2)_7 CH_3$, —C(O)—$(CH_2)_2 CH=CH(CH_2)_7 CH_3$, —C(O)—$(CH_2)_7 CH=CHCH_2 CH=CH(CH_2)_4 CH_3$, or —C(O)—$(CH_2)_2 (CH_2 CH=CH)_4 (CH_2)_4 CH_3$. Each double bond can be in a cis or trans configuration.

In preferred embodiments, the compound is included in a pharmaceutical composition.

A caging group is a group that can be removed from the compound by exposing the compound to light, for example, UV-photolyzable groups that can be removed by a flash of UV. Caging groups are described, for example, in Adams, S. R. and Tsien, R. Y. *Annual Rev. Physiology* 55:755–784 (1993), incorporated herein by reference. The caging group can be 2-nitrobenzyl, 1-(2-nitrophenyl)ethyl, 4,5-dimethoxy-2-nitrobenzyl, 6-nitropiperonyl, 4-hydroxyphenacyl, 7-hydorxycoumarin-4-ylmethyl, or a derivative thereof.

In another aspect, the invention features a method of delivering a phosphoinositide to a cell. The method includes contacting a cell with a membrane-permeant phosphoinositide, transporting the membrane-permeant phosphoinositide into the cell, and converting the membrane-permeant phosphoinositide to a phosphoinositide within the cell.

In another aspect, the invention features a method for identifying a biological process within a cell triggered by intracellular phosphoinositide. The method includes contacting a cell with a membrane-permeant phosphoinositide, transporting the membrane-permeant phosphoinositide into the cell, converting the membrane-permeant phosphoinositide to a phosphoinositide within the cell, and measuring an effect of the phosphoinositide on a biological process. The phosphoinositide can directly affect the biological process, or a metabolite of the phosphoinositide can effect the biological process.

Transporting a membrane-permeant phosphoinositide into the cell can include active transport, passive transport, or diffusion.

The membrane-permeant phosphoinositides can be delivered exogenously to its site of action inside intact cells. $PIP_3$ has at least four negative charges at physiological pH. Therefore, $PIP_3$ is extremely unlikely to diffuse into cells by itself and effective administration of $PIP_3$ itself to intact cells is problematic. A membrane-permeant phosphoinositide is a neutral molecule that can cross the plasma membrane by passive diffusion. Thus, an example of a membrane-permeant phosphoinositide can be $PIP_3$ having the phosphate groups derivatized with acetoxymethyl (AM) groups. The resulting acetoxymethyl phosphate esters can be readily hydrolyzed by intracellular esterases, thereby regenerating $PIP_3$ inside the cells.

Other features or advantages of the present invention will be apparent from the following detailed description and from the claims.

DESCRIPTION OF THE PREFERRED EMBODIMENTS

Figure 1:
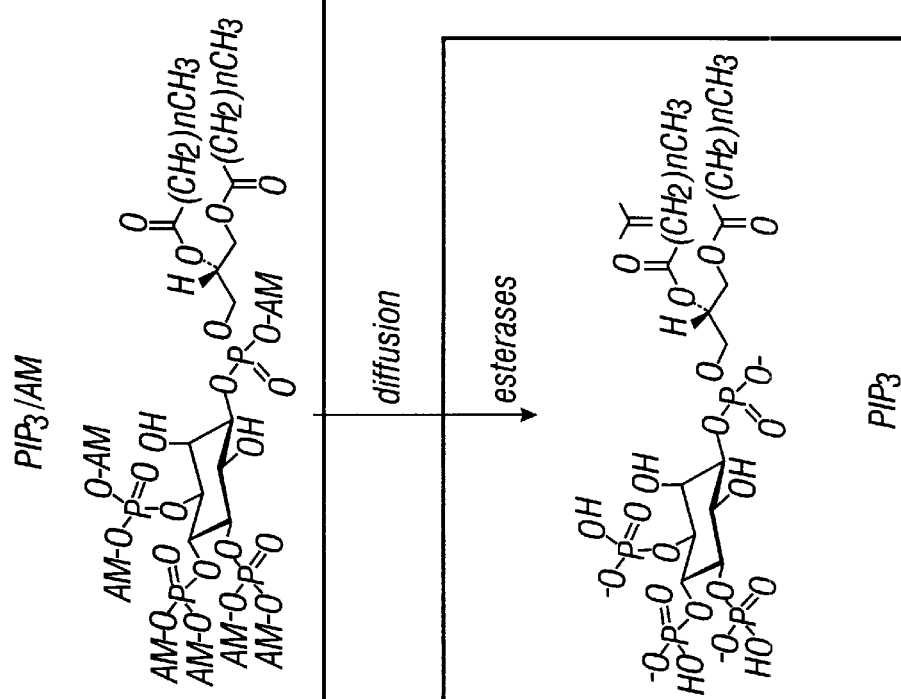
FIG. 1 is a schematic drawing depicting transport of $PIP_3$/AM into cells and its conversion to $PIP_3$.

In general, the invention features membrane-permeant phosphoinositides that can be converted intracellularly to a corresponding phosphoinositide. The membrane-permeant phosphoinositide is a neutral molecule that can cross the plasma membrane by passive diffusion. For example, a membrane-permeant phosphoinositide can be $PIP_3$ having the phosphate groups derivatized with acetoxymethyl (AM) groups. The resulting acetoxymethyl phosphate esters can be readily hydrolyzed by intracellular esterases, thereby regenerating $PIP_3$ inside the cells.

To form a membrane-permeant phosphoinositide, all the phosphate negative charges of $PIP_3$ were esterifies. It is also possible to prepare a membrane-permeant $PIP_3$ derivative in which the 2- and 6-hydroxyls are protected. The 2- and 6-hydroxyls can be protected with hydrolyzable groups such as AM groups. Alternatively, they can be protected to form UV-photolyzable caging groups such as 3,4-dimethoxy-2-nitrobenzyl, 2-nitrobenzyl, 1-(2-nitrophenyl)ethyl, 6nitropiperonyl 4-hydroxyphenacyl, or 7-hydroxycoumarin-4-ylmethyl esters. For example, the 3,4-dimethoxy-2nitrobenzyl group of a corresponding either can be instantaneously removed with a flash of UV, making it an suitable group for unleashing the immediate actions of this fast-acting, rapidly metabolized messenger.

The acyl chain can be derived from a fatty acid. The chain length can be selected to provide compounds that are more soluble or tractable. For example, Reddy, K. K., et al. *J. Org. Chem.* 60:3385–3390 (1995), have shown that di-$C_8$-$PIP_3$ was more soluble and tractable than $PIP_3$'s having chain lengths of $C_{18}$ or $C_{20}$. Because the diacylglycerol group can be added intact at a late stage of the synthesis, this part of the molecule can be varied relatively easily.

A generalized synthesis of membrane-permeant phosphoinositides is shown in Schemes I–IV. In the schemes: TMS-OTf is trimethylsilyl trifluoromethanesulfonate; TBDPS is tert-butyldiphenylsily; Bz is benzoly; py is pyridine; BOM is benzyloxymethyl; TBAF is tetrabutylammonium fluoride; THF is tetrahydrofuran; DMIPS is dimethylisopropylisily; $^1Pr$ is isopropyl; R is 2-cyanoethyl; Ak is a $C_3$–$C_{21}$ alkyl, alkenyl, or polyene; and R' is a protecting group such as, for example, acetoxymethyl.

The synthesis of membrane-permanent esters of $PIP_3$ (Scheme I) can start with enatiomerically pure D-1-O-(tert-butyldiphenylsily)-3,4,5-O-tribenzoyl-myo-inositol (4') which can be prepared from myo-inositol in 4 stages via 1', 2', and 3' with 30% yield, for example, by the method described in Bruzik, K. S. and Tsai, M. D. *J. Am. Chem. Soc.* 114:6361–6374 (1992). 4' can be prepared with high enantiomeric purity and good yield. The hydroxyls of diol 4' can be protected with benzyloxymethyl (BOM) groups to afford 5', which can be easily removed by hydrogenolysis at the end of the synthesis without affecting the other groups on the product. In 5', the myo-inositol 1-hydroxyl was still protected as a tert-butyldiphenylsily (TBDPS) ether, whose bulk can be important in the regioselective synthesis of 4'. The TBDPS group in 5' can be removed with tetrabutylammonium fluoride to afford 6', which can be silylated with DMIPS (dimethylisopropylsilyl) to give 7'. The benzoate groups on 7' can be removed with KCN in methanol to give triol 8', which can be phosphorylated on the 3, 4, and 5 positions with phosphite esters protected as β-cyanoethyl esters and oxidized to give 9'. The DMIPS protecting group can be cleaved by 2.5% HF to give 10'. The 1-hydroxyl of 10'can be linked to a sn-1,2-diacylglycerol via a phosphite ester and oxidized to afford 11'. Diacylglycerols are available, for example, from Avanti Polar Lipds, Inc. The β-cyanoethyl groups on the phosphates can be removed with anhydrous triethylamine to give 12'. The phosphates of 12' can be esterified with R'-X, where X is a leaving group such as bromide, iodide, or trifluormethanesulfonate, (e.g., bromoethyl acetate) to give 13' to mask all seven potential negative charges, for example, as acetoxymethyl (AM)

esters. The final product 14' (PIP$_3$/MP) can be obtained by hydrogenolysis of the BOM groups to free the 2,6-hydroxyls. Alternatively, the BOM groups can be removed prior to esterification, resulting in R' groups on the 2- and 6-hydroxyls.
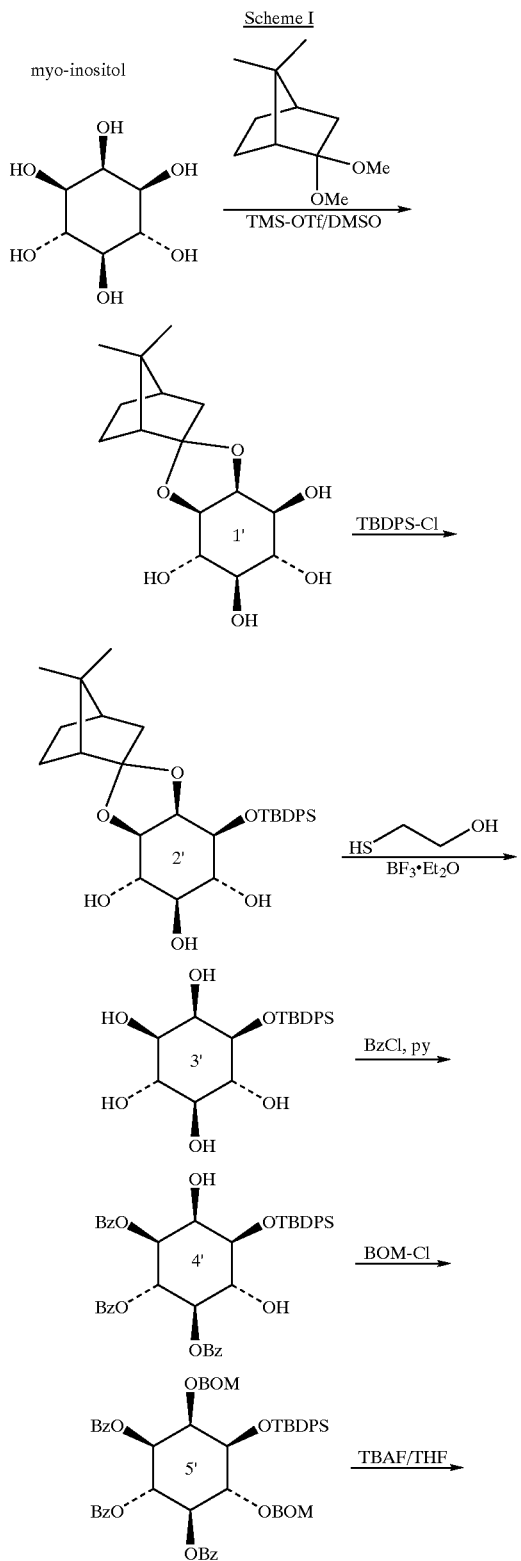
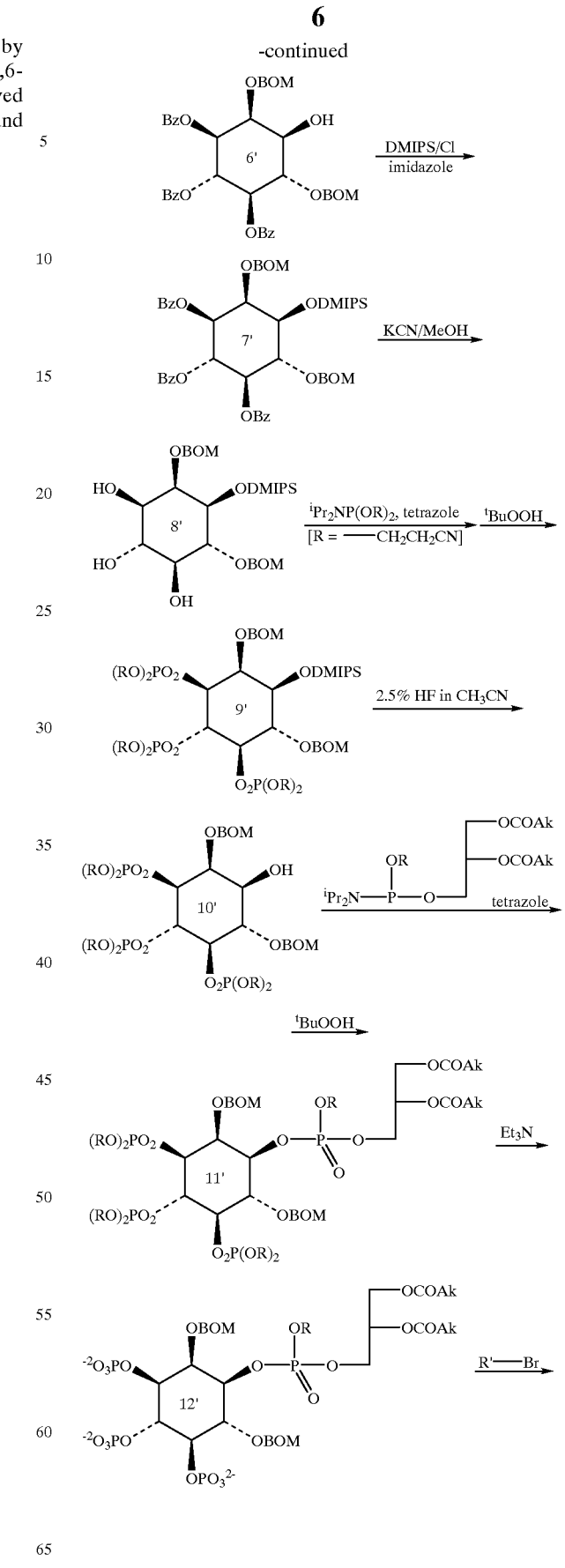

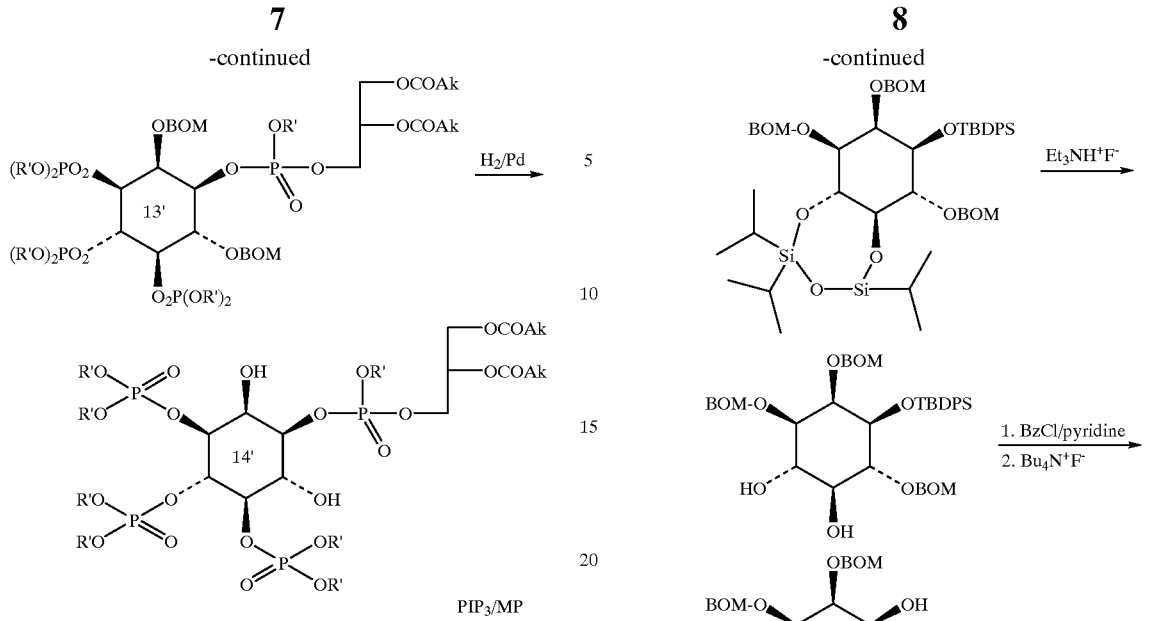

PIP₃/MP

Other derivatives can be prepared by similar methods. For example, thiophosphate analogs can be prepared by oxidizing the phosphite esters with sulfur. In particular, membrane-permeant phosptidylinositol-4,5-diphosphates (PI(4,5)P₂/MP), phosphtidylinositol-3,4-diphosphates (PI(3,4)P₂/MP), and caged phophtidylinositol-4,5-diphosphates (cages PI(4,5)P₂/MP) can be prepared, as shown in Scheme II–IV, respectively. Different protecting groups can be used to produce the different membrane-permeant phosphoinositides.

In Schemes II and III, compounds 20' and 30' can be prepared by the methods described in Bruzik, K. S. and Tsai, M. D. *J. Am. Chem. Soc.* 114:6361–6374 (1992). Generally, the other synthetic steps shown in Schemes II and III are similar to those described for Scheme I.

Scheme II

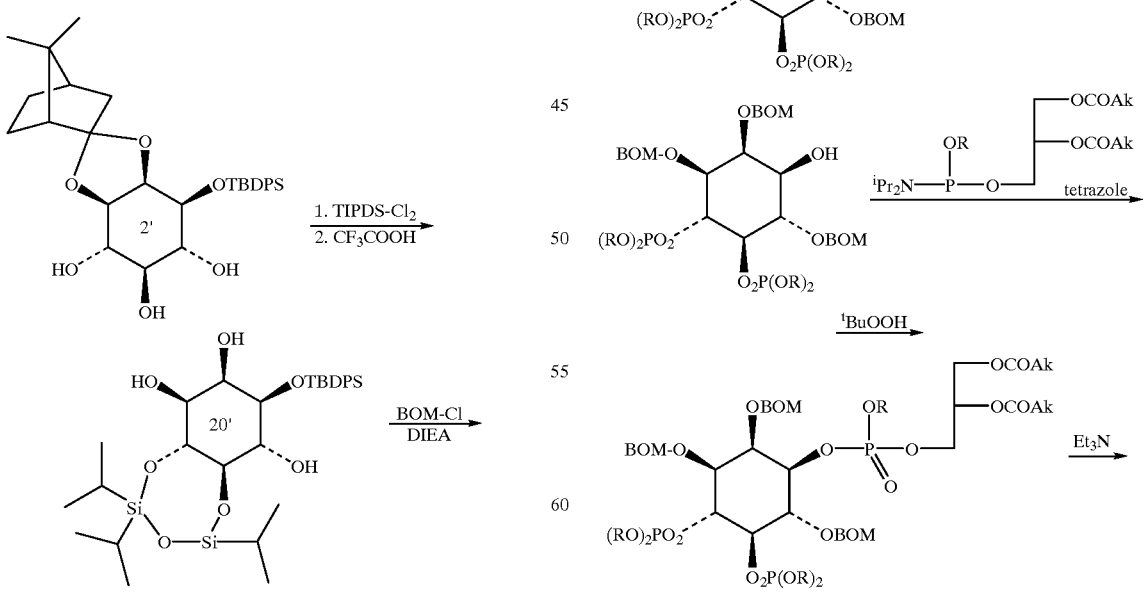

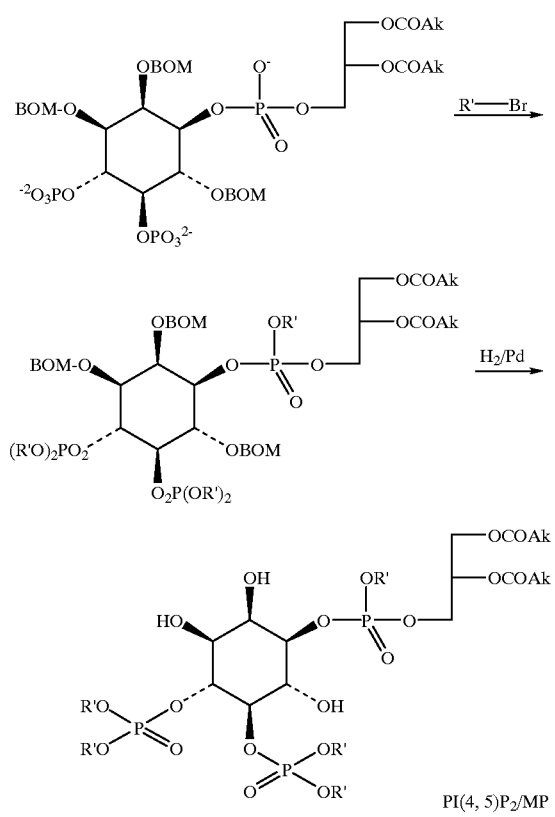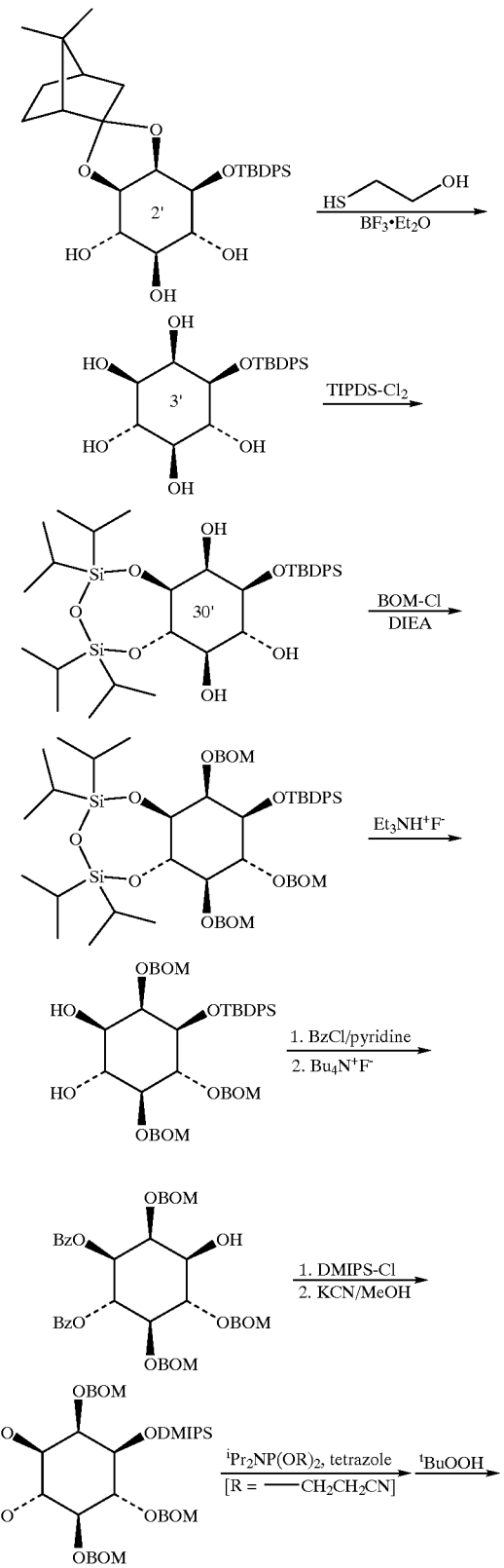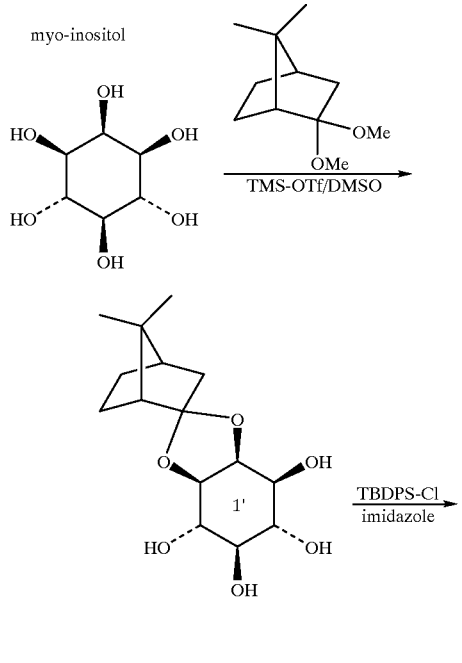

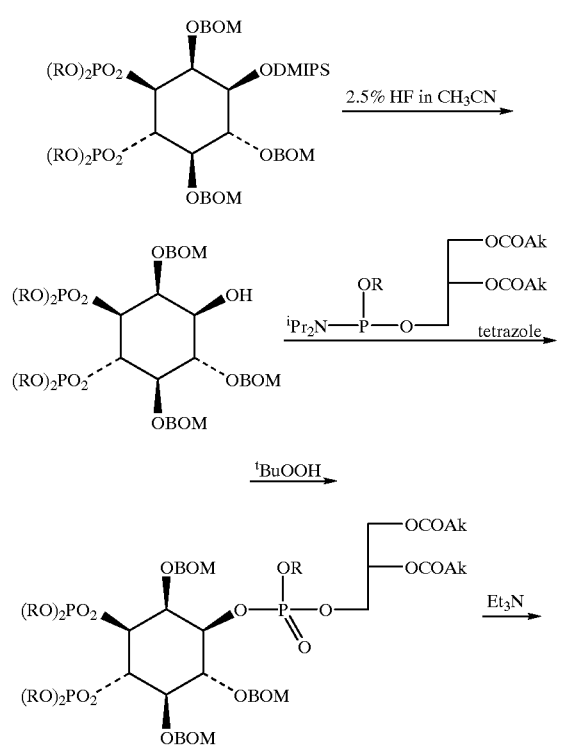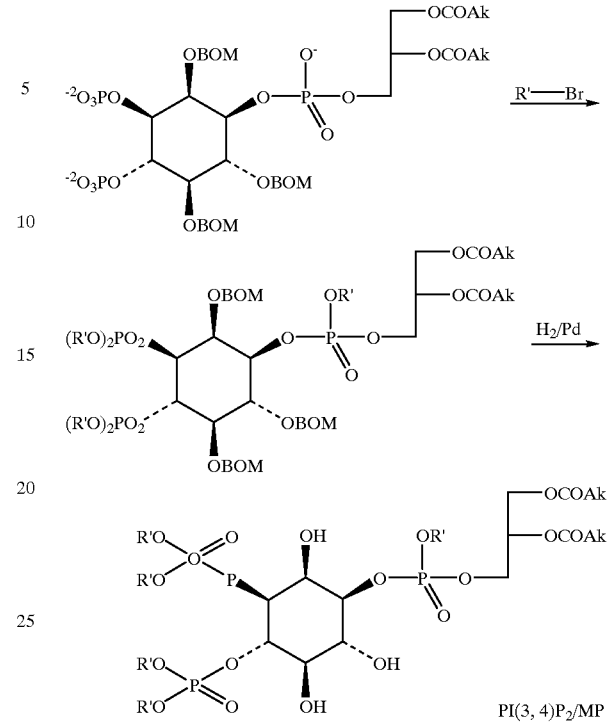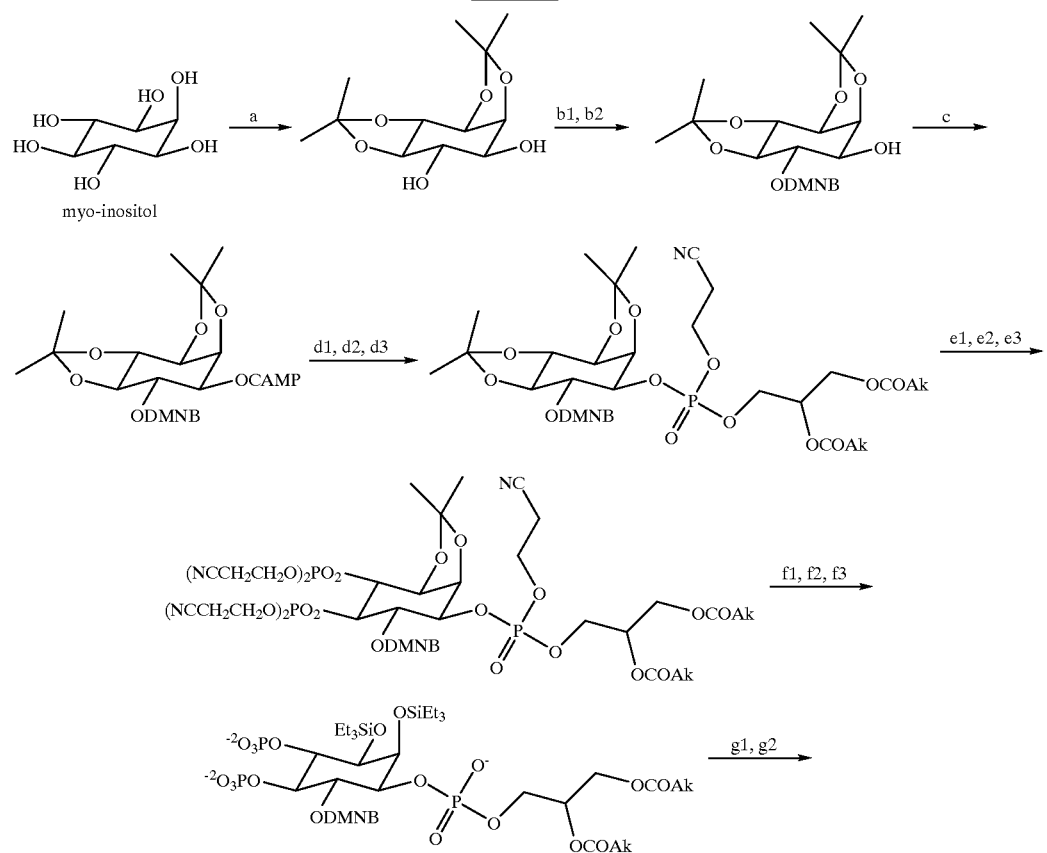

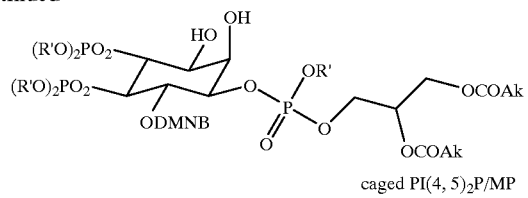

caged PI(4, 5)₂P/MP

The synthesis of one group of caged compounds is shown in Scheme IV. In Scheme IV, step a can be carried out using 2-methoxypropene in acidic DMF; and steps b1 and b2 can be carried out using Bu₂SnO, and tolune azeotropy followed by exposure to 4,5-dimethoxy-2-nitrobenzyl (DMNB) bromide and CsF in DMF. Step c can be carried out by exposure to S-(−)-camphanic (Camp) acid chloride, Et₃N, and 4-dimethylaminopyridine followed by silica gel chromatography and crystallization to separate the diastereomeric camphanates. Steps d1, d2, and d3 can be carried out by exposure of the intermediate to K₂CO₃/MeOH, followed by (i-Pr)₂NP(OCH₂CH₂CH)OCH₂CH(OCOAk) Ch₂OCOAk and tetrazole, which is then followed by exposure to t-BuOOH. Steps e1, e2, and e3 can be carried out by exposure to BF/₃/Et₂O and HSCH₂CH₂OH followed by (i-Pr)₂NP (OCH₂CH₂CN)₂ and tetrazole, and then t-BuOOH. Steps f1, f2, and f3 can be carried by exposure to BF₃/Et₂O and HSCH₂CH₂OH followed by CF₃CON(ME)SiEt₃ and then Et₃N. Steps g1 and g2 can be carried out by exposure to CH₃COOCH₂Br and then Bu₄N³⁰HF₂⁻.

The membrane-permeant phosphoinositides can be applied to intact cells in vitro or in vivo. A cell can be contacted with a membrane-permeant phosphoinositide by exposing the cell to a solution including the membrane-permeant phosphoinositide. The membrane-permeant phosphoinositide can then diffuse or be transported into the cell. Once absorbed into a cell, a membrane-permeant phosphoinositide can be converted into the charged phosphoinositide. When caging groups are present, photolysis can remove the groups to generate the phosphoinositide.

Once converted into a phosphoinositide, biological processes that can be triggered by phosphoinositide can be observed. The biological process can be enhanced or inhibited by the phosphoinositide. The effect of the phosphoinositide, or metabolite thereof, on the biological process can be measured by, for example, an assay designed to monitor the process.

For example, the membrane-permeant phosphoinositides can be a reliable means to introduce the phosphoinositides into intact cells. Once introduced, the physiological roles of the phosphoinositides can be observed. In particular, the specificity of pharmacological inhibitors of kinases can be tested. In specific examples, a membrane-permeant phosphoinositide can deliver phosphatidylinositol-3,4,5-trisphosphate across cell membranes of adipocytes and T₈₄ colon carcinoma cells. The effects of the phosphoinositide can be measured, for example, by monitoring hexose uptake, chloride secretion, or potassium ion efflux. Other biological processes that can also be monitored. Esters of phospholipids can help reveal which interconversions occur inside cells and which lipids are the proximal agonists for many downstream targets. In addition, thiophosphate derivatives can be employed in other situations because the thiophosphate groups are generally not metabolizable.

A pharmaceutical composition can include an effective amount of the membrane-permeant inositol phosphate. As used herein, an effective amount of the membrane-permeant inositol phosphate is the amount of the compound which, upon administration to cells or a patient, causes a desired result in the cells or patient. For example, administration of an effective amount of the membrane-permeant inositol phosphate can stimulate glucose uptake in cells, or chloride efflux from cells. The effective amount to be administered is typically based on the number of cells being treated, the body surface area, patient weight, or the patient condition. The interrelationship of dosages for animals and humans (based on milligrams per meter squared of body surface) is described by Freireich, E. J. et al., *Cancer Chemother. Rep.*, 50(4):219 (1966). Body surface area may be approximately determined from patient height and weight. See, e.g., *Scientific Tables*, Geigy Pharmaceuticals, Ardsly, N.Y., pages 537–538 (1970). Effective doses can vary, as recognized by those skilled in the art, dependant on route of administration, excipient usage, and the possibility of co-usage with other therapeutic treatments.

The pharmaceutical formulation my be administered via the parenteral route, including subcutaneously, intraperitoneally, intramuscularly, and intravenously. Examples of parenteral dosage forms include aqueous solutions of the active agent, in a isotonic saline, 5% glucose or other well-known pharmaceutically acceptable liquid carrier.

The membrane-permeant inositol phosphate can be formulated into dosage forms for other routes of administration utilizing well-known methods. The pharmaceutical composition can be formulated, for example, in dosage forms for oral administration in a capsule, a gel seal or a tablet. Capsules may comprise any well-known pharmaceutically acceptable material such as gelatin or cellulose derivatives. Tablets may be formulated in accordance with the conventional procedure by compressing mixtures of the membrane-permeant inositol phosphate and a solid carrier, and a lubricant. An example of a solid carriers includes starch. The membrane-permeant inositol phosphate can also be administered in a form of a hard shell tablet or capsule containing, for example, lactose or mannitol as a binder and a conventional filler and a tableting agent.

The carrier in the pharmaceutical composition must be "acceptable" in the sense of being compatible with the active ingredient of the formulation (and preferably, capable of stabilizing it) and not deleterious to the subject to be treated.

Without further elaboration, it is believed that one skilled in the art can, based on the description herein, utilize the present invention to its fullest extent. The following examples are, therefore, to be construed as merely representative, and not limitive, of the remainder of the disclosure. All publications cited in this disclosure are incorporated by reference.

EXAMPLE 1

The synthesis of acetoxymethyl esters of PIP₃ (PIP₃/AM) is summarized in Scheme V. The synthesis started with enantiomerically pure D-1-O-(tert-butyldiphenylsilyl)-3,4,5-O-tribenzoyl-myo-inositol (4). 4 was prepared from myo-inositol in 4 steps with 30% yield according to the method described in Bruzik, K. S. and Tsai, M. D. *J. Am. Chem. Soc.* 114:6361:6374 (1992). The NMR spectra, mass spectrum, and optical rotation of 4 were all consistent with literature report. The two hydroxyl groups of 4 were then protected with benzyloxymethyl (BOM) ether groups by reaction with benzyloxymethylchloride (BOM-Cl) to afford 5. The BCM groups can be easily removed by hydrogenolysis at the end of the synthesis without affecting the other groups on the product.

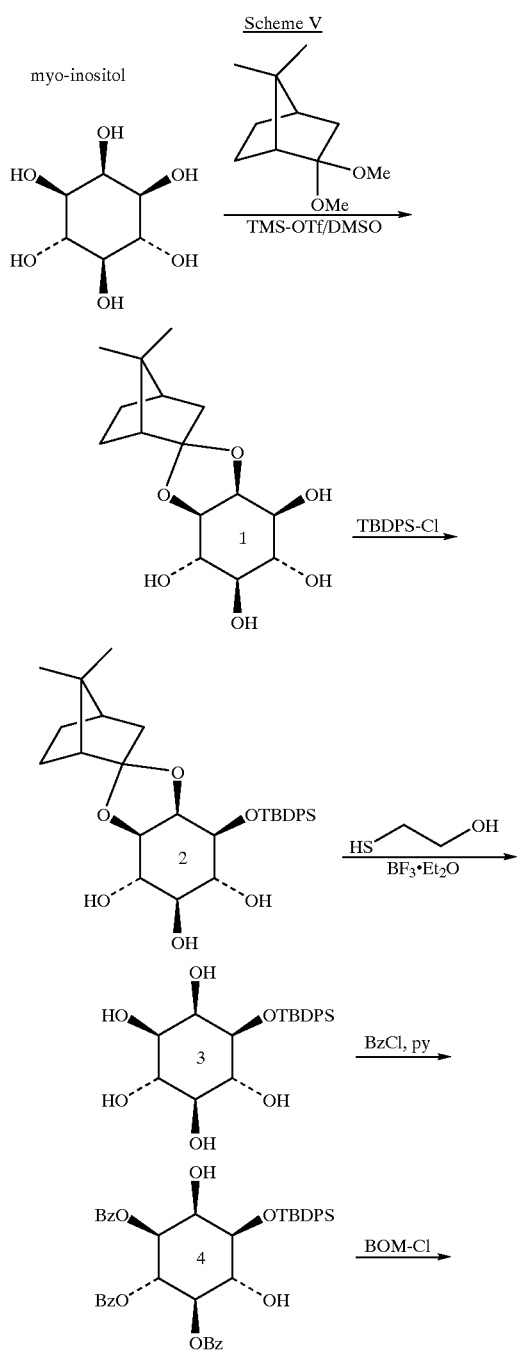

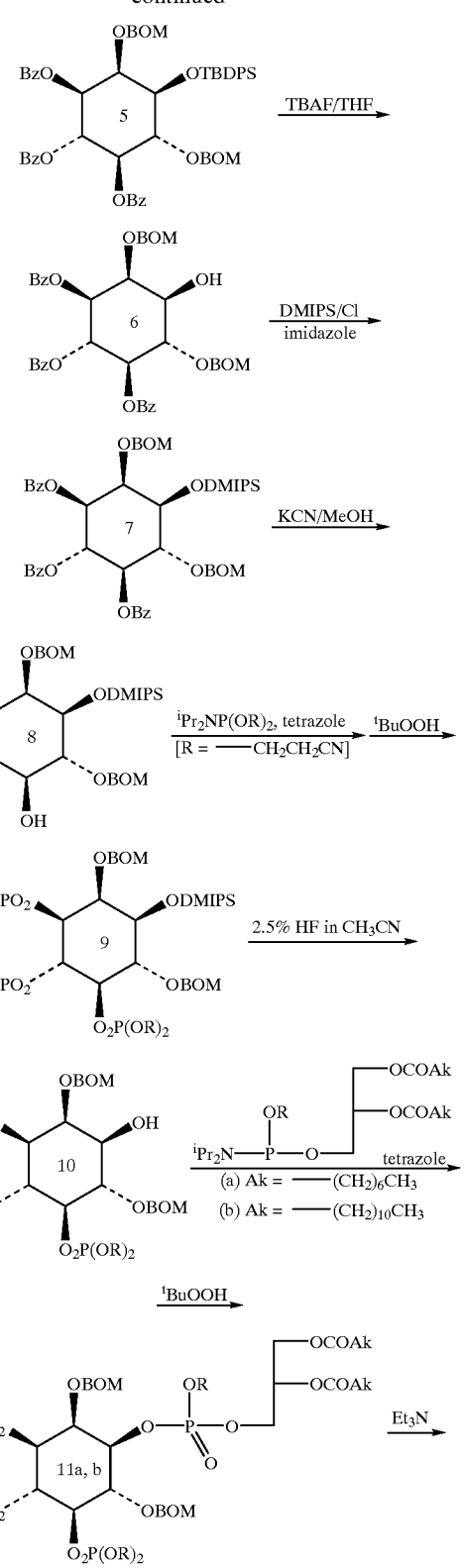

-continued

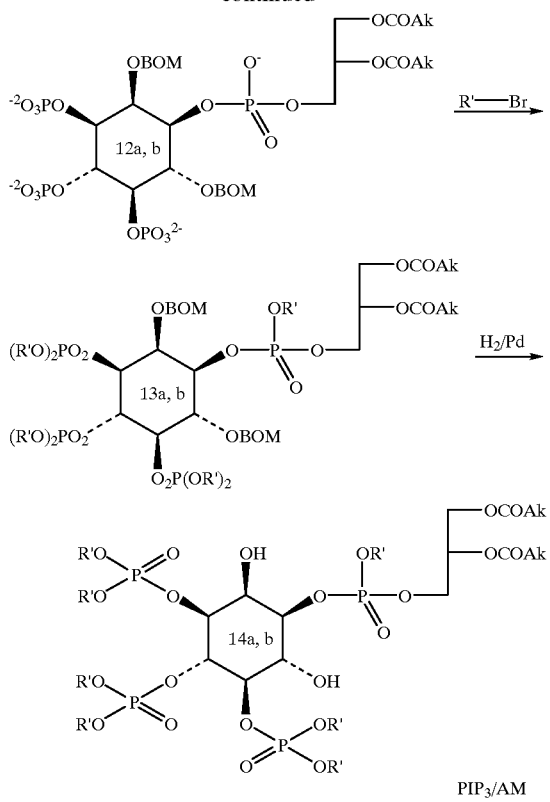

PIP₃/AM

The tert-butyldiphenylsily (TBDPS) group protecting the myo-inositol 1-hydroxyl was removed by treatment of 5 with tetrabutylammonium flouride (TBAF) to afford 6. The myo-inositol 1-hydroxyl was protected by treating 6 with dimethylisopropylsilyl (DMIPS) chloride to afford 7. The benzoyl groups on 7 were removed by treating 7 with KCN in methanol to give triol 8. 8 was then phosphorylated on the 3, 4, and 5 positions and oxidized to 9 by treating 8 with phosphite esters protected with cyanoethoxy groups, followed by oxidation with tert-butyl peroxide. The DMIPS group protecting the 1-hydroxyl or 9 was cleaved by treatment with 2.5% HF to give 10 without affecting the other protecting groups. The 1-hydroxyl of 10 was linked to sn-1,2-dioctanoylglycerol or the analogous dilauroylglycerol to 11a or 11b, respectively by treatment with 10 with 2-cyanoethyl(1,2-diacyl)glyceryl diisopropylchlorophosphoramidite and subsequent oxidation with tert-butyl peroxide. The cyanoethoxy protection groups on the phosphates was removed with anyhdrous triethylamine to 12a or 12b without affecting the diacylglycerol esters. 12a or 12b was esterified with bromomethyl acetate to afford 13a or 13b, thereby masking all seven potential negative charges with acetoxymethyl (AM) groups. The PIP₃/AM compounds 14a and 14b were obtained by hydrogenolysis of the BOM groups to free the 2,6-hydroxyls. For biological comparison, the corresponding di-C₈-PIP₃ lacking the AM groups was prepared by hydrogenolysis of 12a.

All chemicals from commercial sources were used without further purification. Myo-inositol (Aldrich) was dried at 80° C. under high vacuum overnight before use. sn-1,2-Diotanoylglycerol and sn-1,2-dilauroylglycerol were purchased from Avanti Polar Lipids, Inc. Reagents were dried by mixing with activated molecular sieves at least one day before use. $^1$H NMR spectra were obtained on Varian 200 MHz or Bruker 300 MHz instruments. $^{13}$C NMR spectra were obtained at 50 MHz. Mass spectra were recorded on a electrospray mass spectrometer (Hewlett Packard 59987A). Column chromatography was performed on silica gel (230–400 mesh from EM Science).

Snythesis of Compound 5

4 (730 mg, 1 mmol) in dry $CH_2Cl_2$ was treated with 3 mL of diisopropylethylamine (DIEA, 17 mmol) and 1 mL benzyloxymethyl chloride (BOM-Cl, Fluka, 60% purity, 4 mmol) and heated at 60° C. for 30 hours. The reaction mixture was allowed to cool and solvent was removed under vacuum. The brown material was redissolved in $CH_2Cl_2$ and purified by silica gel chromatography, eluting with 6.4 (v/v) $CH_2Cl_2$:hexane. 950 mg colorless oily 5 was obtained, 98% yield. $^1$NMR (CDCl₃, ppm) δ 7.72–7.82 (m, 6H), 7.13–7.48 (m, 29H), 6.31 (t, 1H), 5.59 (t, 1H), 5.03 (dd, 1H), 4,92 (s, 4H), 4.80 (d, 1H), 4.68 (s, 4H), 4.52 (dd, 1H), 4.24 (dd, 1H), (s, 9H); $^{13}$c NMR (CDCl₃, ppm) δ 166.2 159.6, 138.2, 136.4, 133.3, 130.6, 130.4, 130.1, 128.9, 128.7, 128.6, 128.3, 128.2, 127.9, 127.8, 127.7, 97.2, 96.3, 91.8, 74.8, 73.0, 72.0, 71.4, 70.3, 70.1, 27.8, 19.6. Mass spectrum calculated for $C_{59}H_{58}O_{11}Si$=971.2, found 972.2 (positive ion, M +H⁺.

Synthesis of Compound 6

5 (3.5 g, 3.61 mmol) was dissolved in THF and 1.2 g tetrabutylammonium fluroide (TBAF, 4.6 mmol, 1.27 equiv) was added slowly. After stirring for 20 minutes at room temperature, the reaction was completed and solvent was removed. Silica gel column chromatography eluting with 98.2 v/v $CHCl_3$:$CH_3OH$ furnished 2.48 g of 6, 94% yield. $^1$H NMR (CDCl₃, ppm) δ 7.65–7.88 (m, 6H), 7.01–7.48 (m, 19H), 6.08 (t, 3H), 5.53 (t, 1H, 5.22 (dd, 1H), 4.92 (d, 1H), 4.82 (d, 1H), 4.34–4.72 (m, 10H), 4.08 (t, 1H); $^{13}$C NMR (CDCl₃, ppm) δ 166.0, 165.8, 165.7, 137.3, 137.1, 133.4, 133.2, 133.1, 129.8, 129.7, 128.5, 128.4, 128.3, 127.9, 127.8, 127.7, 127.6, 96.2, 80.5, 72.5, 72.0 71.3, 70.5, 70.3, 70.0. Mass spectrum calculated $C_{43}H_{40}O_{11}$=732.8, found 733.7 (positive ion, M+H⁺).

Synthesis of Compound 7

6 (732 mg, 1 mmol) was dissolved in dry dimethylformamide (DMF) with 170 mg imidazole (2.5 mmol). 250 μl dimethylisopropylsilyl chloride (DMIPS-Cl, 1.6 mmol) was added and the reaction mixture stirred under argon at room temperature for 4 hours. DMF was removed under vacuum and the product purified on a silica gel column with $CHCl_3$ as eluant. 7 was obtained as 800 mg colorless, 96% yield. $^1$HMR (CDCl₃, ppm) δ 7.80–7.98 (m, 6H, 7.25–7.48 (m, 19H), 6.24 (t, 1H), 5.68 (t, 1H), 5.28 (dd, 1H), 5.10 (dd, 2H), 4.91 (s, 1H), 4.84 (d, 1H), 4.79 (d, 1H), 4.66 (s, 2H), 4.57 (s, 2H), 4.31 (s, 2H), 4.12 (dd, 1H), 0.96–0.98 (m, 7H), 0.16) d, 6H; $^{13}$C NMR (CDCl₃, ppm) δ 166.2, 138.2, 134.0, 133.6, 130.3, 130.1, 128.9, 128.8, 128.7, 128.6, 127.9, 127.8, 96.4, 96.0, 74.3, 72.8, 72.5, 71.3, 70.2, 69.8, 184, 16.5, -2.2. Mass spectrum: $C_{48}H_{52}O_{11}Si$ calculated 833.0, found 834.0 (positive ion, M+H⁺).

Synthesis of Compound 8

7 (290 mg, 0.35 mmol) was delivered in dry methanol. KCN (100 mg, 1.53 mmol, dried over KOH under vacuum) was added and the reaction mixture was stirred at room temperature for 9 hours. After removing solvent, the reaction mixture was redissolved in $CHCl_3$ and purified on a silica gel column, eluting with 95.5 (v/v) $CHCl_3$;MeOH. 200 mg 8 was obtained, 89% yield. $^1$H NMR (CDCl$_3$, ppm) δ 7.34–7.37 (m, 10H), 5.01 (d, 1H), 4.93 (d, 1H), 4.85 (d, 1H), 4.83 (s, 2H), 4.78 (m, 6H), 4.63 (d, 1H), 4.57 (d, 1H), 4.09 (d, 1H), 3.3.–3.7 (m, 3H), 0.96 (s, 3H), 0.93 (s, 3H), 0.85 (m, 1H), 0.06 (s, 6H); $^{13}$C NMR (CDCl$_3$; ppm) δ 129.1, 128.5, 97.3, 97.2, 85.0, 82.8, 74.3, 74.2, 72.6, 71.5, 70.8, 17.5, 15.3, –2.4. Mass spectrum: C$_{27}$H$_{40}$O$_8$Si calculated 520.7, found 521.8 (M+H$^+$).

Synthesis of Compound 9

2-Cyanoethyl diisopropylchlorophosphoramidite (0.5 g, 2.1 mmol) in dry CH$_2$Cl$_2$ was mixed with 0.4 mL DIEA (1.1 eg) and 160 μL (2.34 mmol) 2-cyanoethanol. After stirring for 30 minutes at room temperature, solvent was removed and dry ethyl ether added to precipitate diisoproplethylammonium chloride. The ether extract containing bis(2-cyanoethyl) diisopropylphosphoramite was mixed with 110 mg of triol 8 (0.17 mmol), then the ether was removed under vacuum. The mixture was redissolved in dry CH$_2$Cl$_2$ and 160 mg 1H-tetrazole (1.1 equiv) added. After stirring overnight at room temperature under argon, 1 mL of 5 M tert-butyl hydroperoxide in hexane was added at 0° C. and stirred 10 minutes at that temperature and then for 2 hours at room temperature. The product was purified on a silica gel column, eluting with 95.5 v/v CHCl$_3$:CH$_3$OH. 200 mg 9 was obtained, 97% yield. $^1$H NMR (CDCl$_3$, ppm) δ 7.32–7.42 (m, 10H), 4.55–5.22 (m, 10H), 4.18–4.50 (m, 15H), 4.08 (t, 1H), 2.82 (t, 12H). Mass spectrum: C$_{45}$H$_{61}$N$_6$O$_{17}$P$_3$Si calculated 1079, found 1102 (M+Na$^+$).

Synthesis of Compound 10

9 (100 mg) was added to 5 mL acetonitrile containing 2.5% aqueous HF and stirred at room temperature for 2 hours. After removing solvent, the product was purified on a silica gel column eluted with 95.5 v/v CHCl$_3$:CH$_3$OH. 85 mg 10 was obtained, 94% yield. $^1$H NMR (CDCl$_3$, ppm) δ 7.30–7.40 (m, 10H), 5.05 (dd, 2H), 4.86 (s, 2H), 4.84 (d, 2H), 4.82 (s, 2H), 4.78 (t, 1H), 4.64 (s, 2H), 4.63 (d, 2H), 4.22–4.48 (m, 13H), 3.89 (t, 1H), 2.78–2.80 (m, 12H); $^{13}$C (CDCl$_3$; ppm) δ 138.2, 137.4, 129.1, 129.0, 128.5, 117.8, 117.6, 117.0, 97.8, 97.5, 82.2, 67.9, 67.6, 67.3, 63.2, 63.1, 20.2, 20.0. Mass spectrum: C$_{40}$H$_{49}$N$_6$O$_{17}$P$_3$ calculated 978.4, found 979.4 (M+H$^+$).

Snythesis of Compound 11a sn-1,2-Dioctanoylglycerol (80 mg, 0.23 mmol) in CH$_2$Cl$_2$ was mixed with 45 μL DIEA and 55 μL 2-cyanoethyl diisopropylchlorophosphoramidite. After stirring for 8 hours at room temperature, solvent was removed and dry ether was added. The crude ether extract of 2-cyanoethyl (1,2-dioctanoyl)glyceryl diisopropylchlorophosphoramiditie was mixed with 100 mg 5 (0.1 mmol) and 100 mg tetrazole (1.4 mmol) and kept at room temperature overnight. 150 μL 5 M tert-butylhydroperoxide was then added. Two hours later, solvent was removed and product was purified on a silica gel column eluted with 98:2 v/v CHCl$_3$:CH$_3$OH. 120 mg 11a was obtained, 82% yield. $^1$H NMR (CDCl$_3$, ppm) δ 7.32–7.42 (m, 10H), 5.42 (q, 1H), 5.05 (dd, 4H), 4.82 (d, 1H), 4.65–4.80 (m, 7H), 4.20–4.50 (m, 15H), 3.91 (t, 1H), 2.70–2.95 (m, 14H), 2.35–2.48 (m, 4H), 1.50–1.72 (m, 8H), 1.18–1.38 (m, 16H), 0.80–0.96 (m, 6H), $^{13}$C (CDCl$_3$, ppm) δ 173.8, 173.6, 138.2, 137.6, 128.9, 128.5, 128.2, 117.7, 117.5, 117.2, 97.6, 97.4, 71.1, 68.7, 66.7, 63.5, 63.2, 62.1, 34.2, 32.0, 29.4, 29.3, 25.2, 22.9, 20.1, 20.0, 19.9, 14.3. Mass spectrum: C$_{62}$H$_{87}$N$_7$O$_{24}$P$_4$ calculated 1438, found 1461 (M+Na$^+$).

Snythesis of Compound 13a 11a (50 mg, 35 μmol) in CH$_2$Cl$_2$ was stirred overnight with 50 μL Et$_3$N at room temperature, then solvent was removed under vacuum. The crude product (12a) was used directly for the next step by dissolving in 1 mL dry acetonitrile and adding 100 μL bromomethyl acetate (1.02 mmol) and 200 μL DIEA (1.15 mmol). The reaction mixture was stirred overnight at room temperature. Solvent was removed and the residue was extracted with dry ethyl ether. The ether supernatant was evaporated and the resulting yellow oil chromatographed on a silica gel column with 98.2 v/v CHCl$_3$:CH$_3$OH. 30 mg 13a was obtained, 55% yield. $^1$H NMR (CDCl$_3$, ppm) δ 7.28–7.42 (m, 10H), 5.52–5.82 (m, 14H), 5.18 (q, 1H), 4.62–4.98 (m, 5H), 4.04–4.42 (m, 8H), 2.04–2.38 (m, 25H), 1.46–1.72 (m, 8H), 1.20–1.42 (m, 16H), 0.82–0.98 (m, 6H). Mass spectrum: C$_{62}$H$_{93}$O$_{38}$P$_4$ calculated 1571, found 1594 (M+Na$^+$).

Synthesis of Compound 14a 15 mg 13a in THF was hydrogenated with 5 mg palladium black for 4 hours at room temperature and atmospheric pressure. After filtering off the catalyst and removing solvent, 4 mg 14a (di-C$_8$-PIP$_3$/AM) was obtained, 96% yield, $^1$H NMR (CDCl$_3$, ppm) δ 5.52–5.80 (m, 14H), 5.18 (q, 1H), 4.64–4.98 (m, 5H), 2.06–2.38 (m, 25H), 1.44–1.74 (q, 1H), 1.20–1.42 (m, 16H), 0.84–0.94 (m, 6H). Mass spectrum: C$_{46}$H$_{79}$O$_{36}$P$_4$ calculated 1330, found 1353 (M+Na$^+$).

Synthesis of Compound 11b 11b was prepared in the same manner as 11, 79% yield. $^1$H NMR (CDCl$_3$, ppm) δ 7.31–7.42 (m, 10H), 5.41 (q, 1H) 5.06 (dd, 4H), 4.80 (d, 1H), 4.64–4.82 (m, 7H), 4.20–4.48 4.48 (m, 15H), 3.92 (t, 1H), 2.68–2.95 (m, 14H), 2.34–2.36 (m, 4H), 1.52–1.72 (m, 12H), 1.17–1.40), (m, 28H), 0.81–0.95 (m, 5H); $^{13}$C NMR (CDCl$_3$, ppm) δ 174.1, 173.8, 138.3, 137.5, 128.8, 128.5, 128.3, 117.8, 117.4, 117.2, 97.5, 97.3, 71.2, 68.8, 66.8, 63.4, 63.2, 62.1, 34.1, 31.9, 29.6, 29.4, 25.3, 22.9, 20.2, 20.1, 20.0, 19.9, 19.8, 14.3. Mass spectrum: C$_{70}$H$_{103}$N$_7$O$_{24}$P$_4$ calculated 1550, found 1573 (M+Na$^+$).

Synthesis of Compound 13b 12b and 13b were prepared in the same manner as 12a and 13a. 12a was used directly for synthesis of 13b without purification. 52 mg of 13b was obtained in 48% yield. $^1$H NMR (CDCl$_3$, ppm) δ7.26–7.41 (m, 10H), 5.52–5.83 (m, 14H), 5.17 (q, 1H), 4.63–5.00 (m, 5H), 4.05–4.45 (m, 8H), 2.05–2.40 (m, 25H), 1.44–1.74 (m, 12H), 1.19–1.44 (m, 28H), 0.82–0.98 (m, 6H). Mass spectrum: C$_{70}$H$_{109}$O$_{38}$P$_4$ calculated 1683, found 1706 (M+Na$^+$).

Synthesis of Compound 14b 14b was prepared in the same manner as 14a. 40 mg 14b (di-C$_{12}$-PIP$_3$/AM) was obtained in 95% yield. $^1$H NMR (CDCl$_3$, ppm) δ 5.51–5.79 (m, 14H), 5.16 (q, 1H), 4.65–4.96 (m, 5H), 2.02–2.41 (m, 25H), 1.45–1.74 (m, 12H), 1.17–1.46 (m, 28H), 0.83–0.92 (m, 6H). Mass spectrum: C$_{56}$H$_{93}$O$_{36}$P$_4$ calculated 1442, found 1465 (M+Na$^+$).

EXAMPLE 2

Glucose Transport

Insulin stimulated uptake of glucose into muscle and fat tissue plays a central role in the maintenance of whole body glucose homeostasis. See, Kahn, C. R. *Diabetes* 45:1644–1654 (1996). The signal transduction pathway utilized by insulin to promote glucose transport involves autophosphorylation of the insulin receptor with ensuing activation of its intrinsic receptor tyrosine kinase activity and phosphorylation of insulin receptor substrates such as IRS-1, IRS-2, IRS-3. See, for example, Cheatham, B. and Kahn, C. R. *Endocrine Reviews* 6:117–142 (1995); and Yenush, L. and White, M. F. *BioEssays* 19:491–500 (1997). PI 3-Kinase interacts with tyrosine-phosphorylated IRS proteins through an SH2 domain on its regulatory p85 subunit, thereby activating its catalytic p110 subunit. See, for example Myers, M. G., Jr. et al. *Proc. Natl. Acad. Sci. USA* 89:10350–10354 (1992); and Shoelson, S. E., et al. *EMBO J.* 12:795–802 (1993). The inhibitors wortmannin and LY294002 have been used in experiments to show that PI 3-kinase is essential for insulin regulation of glucose transport. See, for example, Okada, T., et. al., *J. Biol. Chem.* 269:3568–3573 (1994); and Cheatham, B., et al. *Mol. Biol. Cell* 14, 4902–4911 (1994), respectively.

The impact of PI 3-kinase stimulation on glucose transport is mediated either directly by the D-3-phosphorylated inositol phospholipid products of the enzyme, or by activation of intermediate molecules. Because of the known pharmacology of 3T3-L1 adipocytes and the importance of insulin-stimulated glucose transport in these cells, they were used to test the effects of the membrane-permeant, $PIP_3$ esters on the glucose uptake in adipocytes. In particular, the ability of the membrane-permeant $PIP_3$ esters to bypass wortmannin blockade was examined.

Adiopocyte Cell Culture

All cell culture solutions and supplements were obtained from Gibco/BRL (Burlington, ON, Canada). 3T3-L1 cells were obtained from the University of Bath, England and were grown in monolayer culture in 12-well plates, bathed in Dulbecco's modified Eagle's medium (DMEM) supplemented with 10% (v/v) calf serum and 1% (v/v) antibiotic solution (10,000 U/mL penicillin and 10 mg/mL streptomycin) in an atmosphere of 5% $CO_2$ at 37° C. The medium was replenished every 48 hours. Prior to experimental manipulation, the cells were depleted of serum for 3 hours.

Determinination of 2-Deoxyglucose Uptake in 3T3-L1 Adipocytes

3T3-L1 adipocyte monolayers were rinsed with 140 mM NaCl, 2.4 mM $MgSO_4$, 5 mM KCl, 1 mM $CaCl_2$ and 20 mM Na-HEPES, at pH 7.4. Glucose uptake was measured in 0.25 mL incubation volumes using 10 $\mu$M 2-[$^3$H]deoxyglucose (1 $\mu$Ci/mL; New England Nuclear) for 5 minutes. 2-Deoxyglucose uptake is generally linear during this exposure time period. The radioactive solution was aspirated, and the cells were rinsed three times with ice-cold isotonic saline solution. Cells were disrupted with 1.0 mL of 0.05 N NaOH, and the radioactivity of a 0.75 mL aliquot of the cell lysate was quantitated by liquid scintillation counting using an LKB 1217 beta counter. Protein concentration of the lysate was determined using the Bradford method. See Bradford, N. M. *Anal. Biochem.* 72:247–254 (1976). Nonspecific uptake was determined in the presence of 10 $\mu$M cytochalasin B (Sigma) and was suptracted from total uptake.

Effects on Glucose Uptake into 3T3-L1 adipocytes

Figure 2:
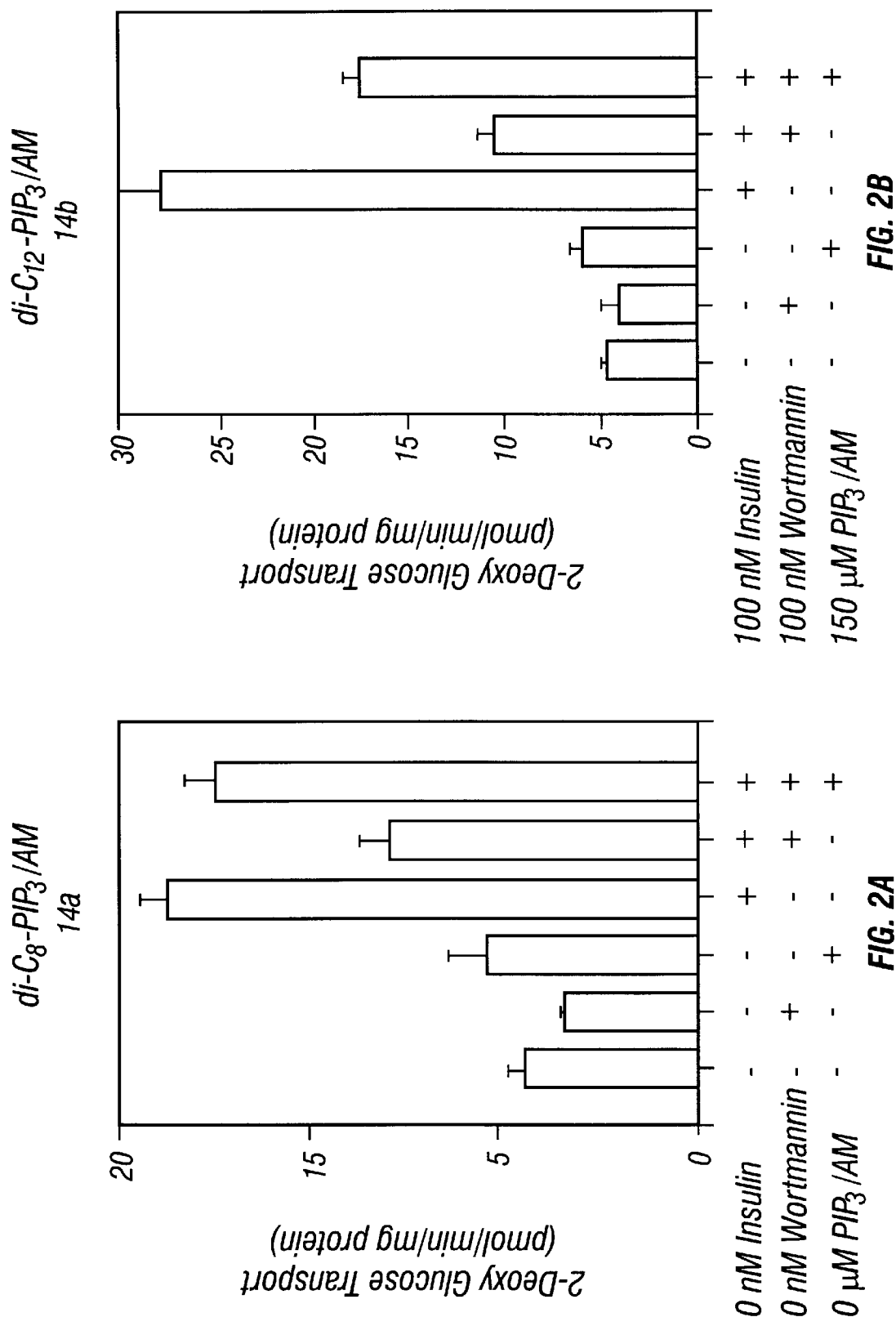
FIG. 2 is a graph depicting the effects of insulin, wortmannin, and $PIP_3$/AM on hexose uptake in adipocytes. The adipocytes were incubated in the presence (+) or absence (−) of the agents listed below each bar.

Glucose uptake into adipocytes was markedly stimulated by a maximally effective dose of insulin. Referring to FIG. 2, the graphs summarize the effects of insulin, wortmann, and $PIP_3$/AM on hexose uptake in adipocytes. The adipocytes were incubated in the presence (+) or absence (−) of the agents (insulin, wortmannin, or $PIP_3$/AM) listed below each bar. Insulin (100 mM) was added to the adiopocytes 30 minutes before measurement of deoxyglucose uptake. $PIP_3$/AM (14a or 14b) (150$\mu$M) and wortmannin (100 mM) were added for a 15 min pre-incubation before insulin treatment. The left and right panels of FIG. 2 indicate experiments using di-$C_8$-$PIP_3$/AM (14a) and di-$C_{12}$-$PIP_3$/AM (14b), respectively.

Referring to FIG. 2, the increase in glucose uptake was inhibited by the PI3K inhibitor wortmannin. Notably, the wortmannin inhibition was largely circumvented by treatment of the cells with the membrane-permeant phosphoinositide $PIP_3$/AM. Di-$C_8$ $PIP_3$/AM (14a) restored a greater percentage (87%) of the insulin stimulation than di-$C_{12}$ $PIP_3$/AM (14b), which restored 56% of the insulin stimulation. Neither $PIP_3$/AM had a significant effect on glucose uptake in the absence of insulin.

The membrane permeable inositol phosphates alone did not stimulate basal glucose transport. A bifurcation of the insulin induced signal can occur in which one signal involves generation of $PIP_3$, while the other is independent of this product. Full stimulation of glucose transport would require activation of both signals. For example, the transport can depend on two enzymes whose activity was recently shown to depend prior PI3K activation: the protein kinase c-Akt (also known as PKB) and protein kinase C-ζ.

The membrane-permeant inositol phosphate esters can be useful to study the PI3K product and insulin action.

EXAMPLE 3

Chloride Flux

Regulation of chloride flux plays a key role in a number of biological systems, including in the control of salt and fluid secretion across mucous membranes. Epithelial transport can be modelled using the $T_{84}$ colon carcinoma cell line which forms monolayers that actively transport chloride in response to a variety of agonists. For example, chloride secretion in $T_{84}$ cells can be triggered through cyclic AMP and calcium-dependent signaling mechanisms. For example, Weymer, A., et al. *J. Clin. Invest.* 76, 1828–1836 (1985); and Dharmsathaphorn, K. et al. *Am. J. Physiol.* 256, C1224–1230 (1989). As in many other systems, these pathways interact synergistically in $T_{84}$. See, for example, Cartwright, C. A., et al. *J. Clin. Invest.* 76, 1837–1842 (1985); MacVinish, L. J., et al. *Br. J. Pharmacol.* 108, 462–468 (1993); and Vajanaphanich, M., et al. *J. Clin. Invest.* 96, 386–393 (1995).

Two receptor activated pathways have been recently identified which limit chloride secretion through the calcium-dependent pathway, but not through the cyclic AMP-dependent pathway. In one pathway, prolonged stimulation of the muscarinic $M_3$ receptor on $T_{84}$ cells leads to accumulation of intracellular inositol-3,4,5,6-tetraphosphate, which, in turn, inhibits transepithelial chloride efflux by restricting flow through apically located chloride channels. See, for example, Vajanaphanich, M., et al. *Nature* 371:711–714 (1994). Another pathway, which is stimulated by EGF and inhibited by wortmannin, also restricted transepithelial chloride transport by limiting basolateral efflux through potassium ion channels. Moreover, the effects of EGF and carbachol are additive, further indicating that the two inhibitory pathways are independent. EGF probably partly works through stimulation of PI3K, because EGF treatment elevates $PIP_3$, and the effect of EGF can be ablated by the PI3K inhibitor wortmannin. See, for example, Uribe, J. M., et al. *J. Biol. Chem.* 271, 26588–26596 (1996); Barrett, K. E., et al. *Am J. Physiol.* (1998); and Eckmann, L., et al. *Proc. natl. Acad. Sci. USA* 94, 14456–14460 (1997). The previous experiments did not address whether the wortmannin block is specific and whether EFG might also have other biochemical effects that are also necessary for its inhibition of carbachol-stimulated chloride flux. We tested whether either $PIP_3$/AM or $PIP_3$ could mimic the effect of EGF on chloride transport in the $T_{84}$ colon carcinoma cell.

$T_{84}$ Colon Carcinoma Cell Culture $T_{84}$ cells (passages 15–45) were grown and maintained in DMEM/F12 media (JRH Biosciences, Lexena, Kans.) supplemented with 5% newborn calf serum, 2 mM glutamine and 50 U/mL each of penicillin/streptomycin (Core Cell Culture Facility, University of California, San Diego) as previously described in Dharmsathaphorn, K., et al. *Am. J. Physiol.* 264: G204–G208 (1984). Cells used in experiments were plated on Costar snap-well inserts and maintained in culture for 6–10 days to allow for formation of tight junctions prior to the experiment.

Short Circuit Current Measurements

Snap-well inserts containing confluent $T_{84}$ monolayers were incubated for 0.5 hr at 37° C. with 0.1 mL $PIP_3$ derivaties (200 μM) or vehicle applied to the apical side. The monolayers were then mounted into modified Ussing chambers (Physiologic Instruments, San Diego, Calif.), whose basolateral side was bathed with Ringers solution warmed to 37° C. and gassed continuously with 95% $O_2$/5% $CO_2$ at a rate of 30–35mL/min. The spontaneous potential difference across the monolayer was short-circuited with a voltage clamp (Model VCC MC6, Physiologic Instruments, San Diego, Calif.) Short circuit current ($I_{sc}$) and conductances were recorded at 4 second intervals using Acquire and Analyse Software 1.1. (Physiologic Instruments, San Diego, Calif.). Increased $I_{sc}$ in $T_{84}$ reflects transepithelial chloride secretion. See, Dharmathaphorn, K., et al. *Am. J. Physiol.* 256: C1224–C1230 (1989).

Rubidium Ion Efflux Measurements

Rubidium ion flux measurements were obtained by a modification of a method previously published by Venglarik, et al. *Am. J. Physiol.* 259: 259:C358–C364 (1990). Cell monolayers grown on Costar snap-well inserts (Cambridge, Mass.) were rinsed in Hank's balanced Salt Solution containing sodium ion (137.6 mM), chloride (146.3 mM), potassium ion (5.8 mM), $H_2PO_4^-$ (0.44 mM), $HPO_4 2-$ (0.34 mM), calcium ion (1 mM), magnesium ion (1 mM), HEPES (ph 7.2) (15 mM), and D-glucose (10mM). The cells were loaded for 30 minutes with 5 μCi/0.25 mL of $^{86}Rb$ at 37° C. added to the basolateral surface. Simultaneously, the apical surface was bathed with cell permeant esters of $PIP_3$ (14a or 14b; 200 μM) or other vehicle. Following four rinses of apical and basolateral surfaces with Hank's buffer over a period of six minutes, the inserts were sequentially transferred at two minute intervals to fresh wells of a 24 well culture dish floating in a 37° C. water bath. After twelve minutes, the inserts were transferred to wells containing 0.1 mM carbachol for the remainder of the experiment. After the experiment, the contents of the wells and the inserts were transferred to vials containing Esoscint which were counted in a Packard scintillation counter. The data were analyzed as described by Venglarik, et al. *Am. J. Physiol.* 259:C358–C364 (1990) yielding rate constants of nuclide efflux at two min intervals.

Effects on Chloride Transport Across $T_{84}$ Monolayers $PIP_3$/AM by itself was able to mimic the action of EGF on a model of colonic epithelia. Di-$C_{12}$ $PIP_3$/AM (14b) was more effective than di-$C_8$ $PIP_3$/AM (14a). Extracellular nonesterified $PIP_3$ had no effect, confirming that the site yof action was intracellular and that esterification was necessary for effective transmembrane delivery of $PIP_3$ in this system.

Figure 3:
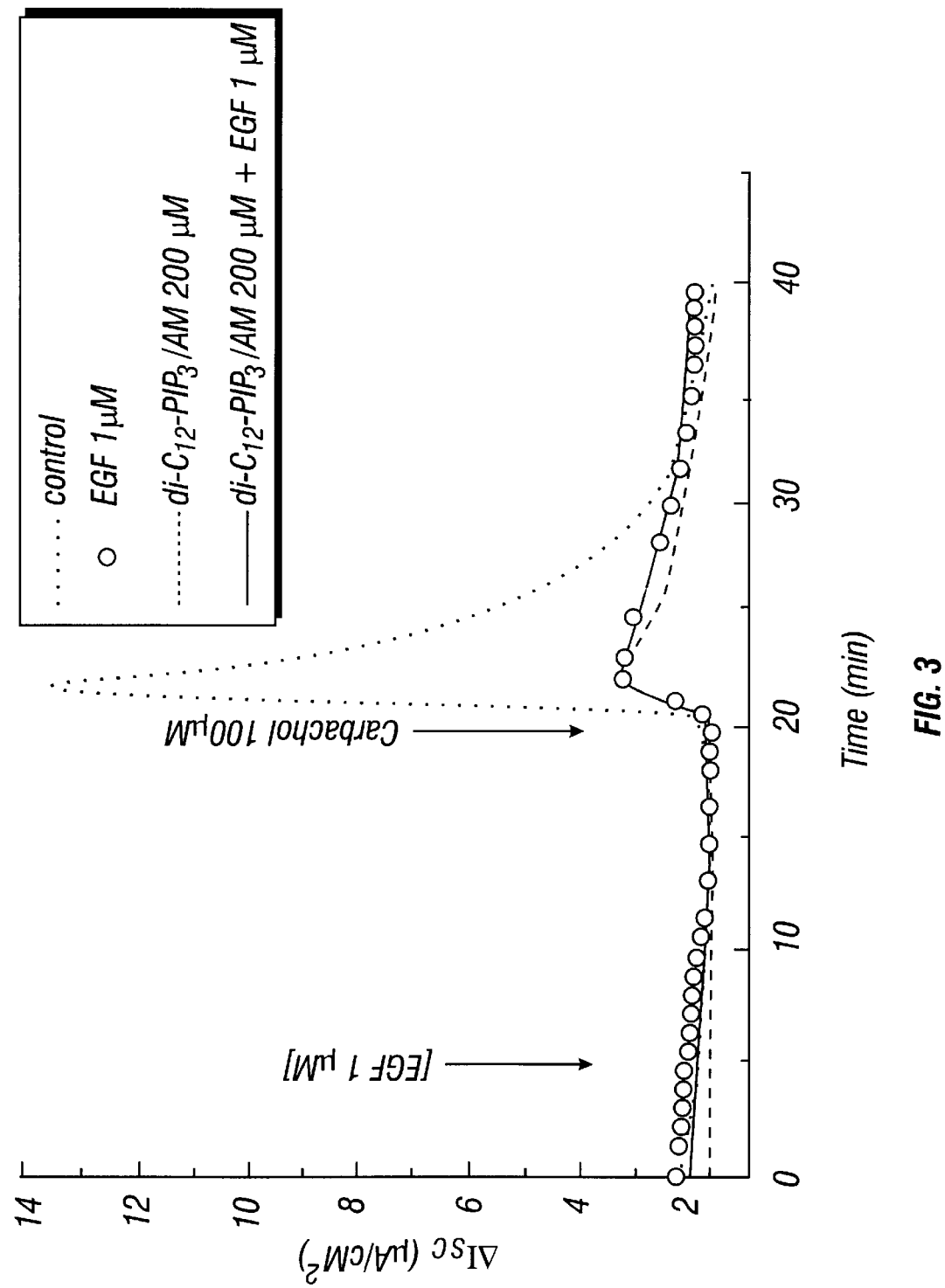
FIG. 3 is a graph depicting the effects of EGF and $PIP_3$/AM on chloride secretion from $T_{84}$ monolayers.

Referring to FIG. 3, the inhibitory effects of EGF and $PIP_3$/AM on chloride secretion are nonadditive. The $T_{84}$ monolayers were incubated for 30 minutes with 200 μM di-$C_{12}$-$PIP_3$/Am or other vehicle prior to mounting in Ussing chambers. Chloride secretion was assessed as short circuit current ($I_{sc}$), which was measured continuously at 4 second intervals. EGF (1 μM) was added to the basolateral surface of some chambers followed 15 minutes later by carbachol (100 μM). Control runs were also stimulated with carbachol but not pretreated with EGF. In FIG. 3, each trace represents the average of six experiments.

Referring to FIG. 3, the traces show the large $I_{sc}$ stimulated by carbachol (dotted line) and its nearly complete inhibition by pretreatment either with 1 μM EGF for 15 min (circles) or with 200 μM di-$C_{12}$-$PIP_3$/AM (14b) for 30 minutes (dashed line). EGF and $PIP_3$/AM were equally effective in reducing carbachol-stimulated peak $I_{sc}$ to 15% of the control. The combination of maximal doses of both EGF and $PIP_3$/AM (solid line) was no more effective than either alone.

Figure 4:
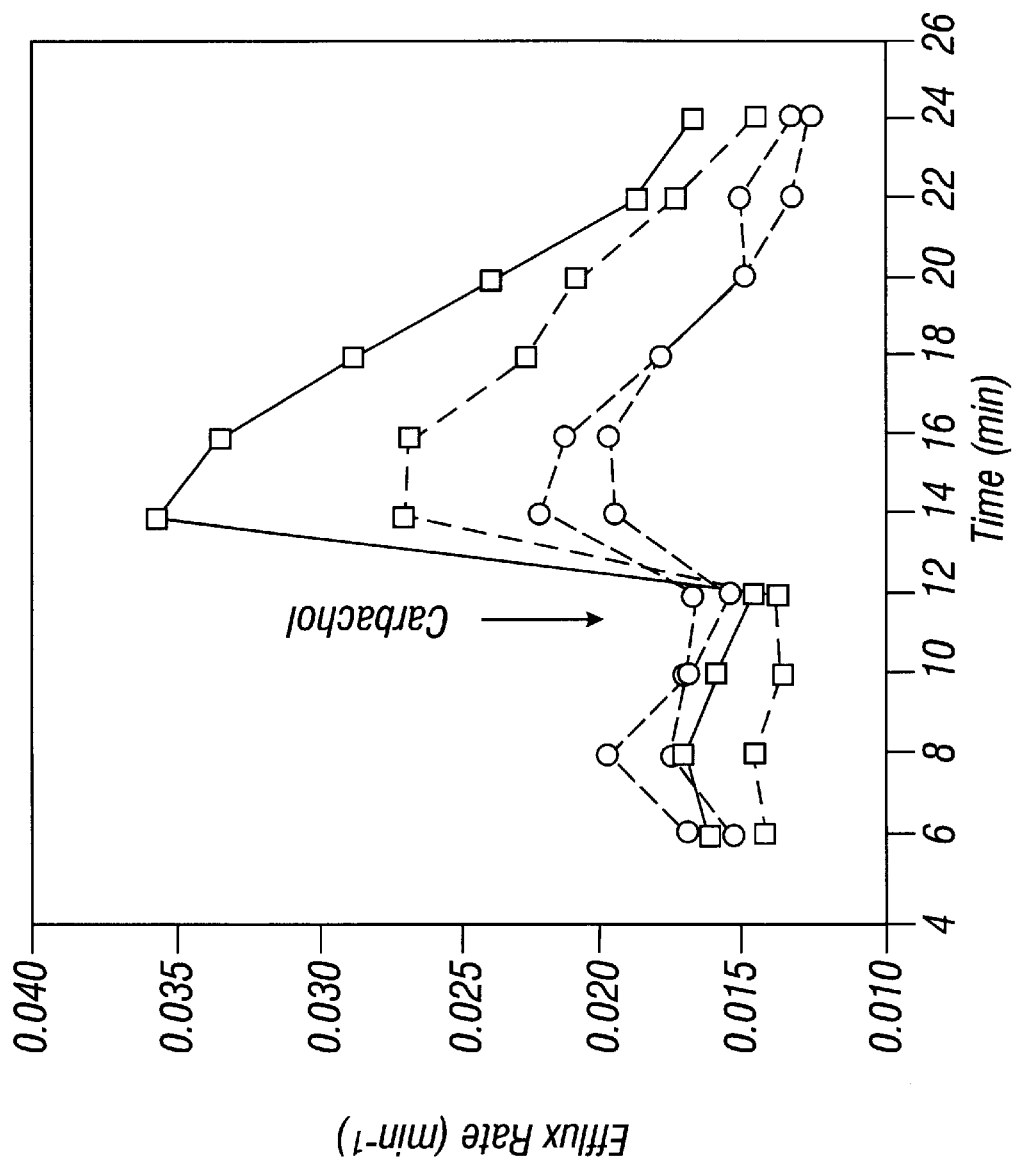
FIG. 4 is a graph depicting the effects of $PIP_3$/AM on $^{86}RB^+$ efflux from preloaded $T_{84}$ colonic epithelia.

An inhibition of the carbachol-stimulated rise in $[Ca^{2+}]_1$ could inhibit $I_{sc}$, but direct imaging of $[Ca^{2-}]_i$ in fura-2-loaded $T_{84}$ monolayers failed to reveal any such effect of $PIP_3$/AM. Transepithelial chloride fluxes can require opening of basolateral $K^+$ channels, whose function can be assayed by measuring efflux of preloaded $^{86}Rb^+$ as a potassium ion surrogate. Referring to FIG. 4, the effects of $PIP_3$/AM on $^{86}Rb^+$ efflux from preloaded $T_{84}$ colonic ephthelia are shown. $T_{84}$ monolayers grown on Millipore inserts were pretreated with either di-$C_{12}$-$PIP_3$/AM (200 μM, circles) or vehicle (squares) for 30 minutes during labeling. The two traces for each set of conditions are replicate experiments. Monolayers were washed and the buffer in the basolateral reservoir was replaced every two minutes. Carbachol (100 μM) was added to the basolateral reservoir at the indicated time. Values are the calculated rate constants at the indicated time points for individual experiments. As shown in FIG. 4, di-$C_{12}$-$PIP_3$/AM (14a) did inhibit carbachol-stimulated $^{86}Rb^+$ efflux by greater than 50 percent. The potassium ion channels are a likely target for the $PIP_3$ effect.

Membrane-permeant esters of $PIP_3$ mimic the inhibitory effects of EGF both on chloride secretion and efflux through potassium ion channels. The data strongly suggest that a lipid product of $PI_{-3}$ kinase mediates EGF-induced inhibition of chloride secretion in $T_{84}$ colonic epithelia.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and, without departing from the spirit and scope thereof, can make various changes and modification of the invention to adapt it to various usages and conditions. Thus, other embodiments are also within the claims.

What is claimed is:

1. A compound of formula:

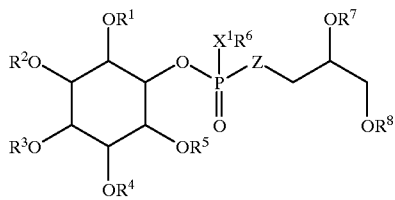

wherein:

R$^1$ is H, —CH$_2$OC(O)CH$_3$, —CH$_2$OC(O)CH$_2$CH$_3$, —CH$_2$OC(O) (CH$_2$)$_2$CH$_3$, or a caging group;

R$^2$ is H, —CH$_2$OC(O)CH$_3$, —CH$_2$OC(O)CH$_2$CH$_3$, —CH$_2$OC(O) (CH$_2$)$_2$CH$_3$, or —P(O) (OR$^{11}$) (X$^2$R$^{12}$), or a caging group;

R$^3$ is H, —CH$_2$OC(O)CH$_3$, —CH$_2$OC(O)CH$_2$CH$_3$, —CH$_2$OC(O) (CH$_2$)$_2$CH$_3$, —(O) (OR$^{13}$) (X$^3$R$^{14}$), or a caging group;

R$^4$ is H, —CH$_2$OC(O)CH$_3$, —CH$_2$OC(O)CH$_2$CH$_3$, —CH$_2$OC(O) (CH$_2$)$_2$CH$_3$, —P(O) (OR$^{15}$) (X$^4$R$^{16}$), or a caging group;

R$^5$ is H, —CH$_2$OC(O)CH$_3$, —CH$_2$OC(O)CH$_2$CH$_3$, —CH$_2$OC(O) (CH$_2$)$_2$CH$_3$, or a caging group;

each of X$^1$, X$^2$, X$^3$, and X$^4$, is, independently, S or O;

each of R$^6$, R$^{11}$, R$^{12}$, R$^{13}$, R$^{14}$, R$^{15}$, and R$^{16}$ is, independently, H, —CH$_2$OC(O)CH$_3$, —CH$_2$OC(O) CH$_2$CH$_3$, or —CH$_2$OC(O) (CH$_2$)$_2$CH$_3$;

each of R$^7$ and R$^8$ is, independently, a saturated or unsaturated C$_4$–C$_{22}$ acyl, a C$_4$–C$_{22}$ alkyl, a C$_4$–C$_{22}$ alkenyl, or a C$_4$–C$_{22}$ polyene.

Z is O, CH$_2$, or NH; and at least one of R$^6$, R$^{11}$, R$^{12}$, R$^{13}$, R$^{14}$, R$^{15}$, and R$^{16}$ is —CH$_2$OC(O)CH$_3$, —CH$_2$OC(O)CH$_2$CH$_3$, or —CH$_2$OC(O) (CH$_2$)$_2$CH$_3$.

2. The compound of claim 1, wherein R$^2$ is —P(O) (OR$^{11}$) (X$^2$R$^{12}$).

3. The compound of claim 1, wherein R$^3$ is —P(O) (OR$^{13}$) (X$^3$R$^{14}$).

4. The compound of claim 2, wherein R$^3$ is —P(O) (OR$^{13}$) (X$^3$R$^{14}$).

5. The compound of claim 1, wherein R$^4$ is —P(O) (OR$^{15}$) (X$^4$R$^{16}$).

6. The compound of claim 3, wherein R$^4$ is —P(O) (OR$^{15}$) (X$^4$R$^{16}$).

7. The compound of claim 4, wherein R$^4$ is —P(O) (OR$^{15}$) (X$^4$R$^{16}$).

8. The compound of claim 1, wherein Z is O.

9. The compound of claim 1, wherein each of X$^1$, X$^2$, X$^3$, and X$^4$ is O.

10. The compound of claim 1, wherein the caging group is 2-nitrobenzyl, 1-(2-nitrophenyl)ethyl, 4,5-dimethoxy-2nitrobenzyl, 6-nitropiperonyl, 4-hydroxyphenacyl, or 7-hydroxycoumarin-4ylmethyl.

11. The compound of claim 1, wherein each of R$^7$ and R$^8$, independently, is —C(O) (CH$_2$)$_m$CH$_3$ where m is an integer between 4–20, inclusive, —C(O)—(CH$_2$)$_7$CH═CH(CH$_2$)$_7$CH$_3$, —C(O)—(CH$_2$)$_7$CH═CH(CH$_2$)$_7$(CH$_3$), —C(O)—(CH$_2$)$_7$CH═CHCH$_2$CH═CH (CH$_2$)$_4$CH$_3$, or —C(O)—(CH$_2$)$_2$(CH$_2$CH═CH)$_4$(CH$_2$)$_4$CH$_3$, wherein each double bond independently, is in a cis or trans configuration.

12. The compound of claim 1, wherein each of R$^6$, R$^{11}$, R$^{12}$, R$^{13}$, R$^{14}$, R$^{15}$, and R$^{16}$ is —CH$_2$OC(O)CH$_3$.

13. The compound of claim 1, wherein at least one of R$^2$, R$^3$, and R$^4$ is a phosphorus-containing group.

14. The compound of claim 1, wherein at least two of R$^2$, R$^3$, and R$^4$ are phosphorus-containing groups.

15. The compound of claim 1, wherein R$^2$, R$^3$, and R$^4$ are phosphorus-containing groups.

16. A pharmaceutical composition of the compound of claim 1.

17. The compound of claim 1 of the formula:

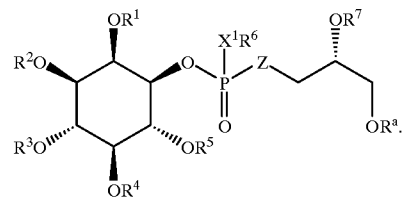

18. The compound of claim 17, wherein R$^2$ is —P(O) (OR$^{11}$) (X$^2$R$^{12}$).

19. The compound of claim 17, wherein R$^3$ is —P(O) (OR$^{13)\,(X^3}$R$^{14}$).

20. The compound of claim 18, wherein R$^3$ is —P(O) (OR$^{13}$) (X$^3$R$^{14}$).

21. The compound of claim 17, wherein R$^4$ is —P(O) (OR$^{15}$) (X$^4$R$^{16}$).

22. The compound of claim 19, wherein R$^4$ is —P(O) (OR$^{15}$) (X$^4$R$^{16}$).

23. The compound of claim 20, wherein R$^4$ is —P(O) (OR$^{15}$) (X$^4$R$^{16}$).

24. The compound of claim 17, wherein Z is O.

25. The compound of claim 17, wherein each of X$^1$, X$^2$, X$^3$, and X$^4$ is O.

26. The compound of claim 17, wherein the caging group is 2-nitrobenzyl, 1-(2-nitrophenyl)ethyl, 4,5-dimethoxy-2-nitrobenzyl, 6-nitropiperonyl, 4-hydroxyphenacyl, or 7-hydroxycoumarin-4-ylmethyl.

27. The compound of claim 17, wherein each of R$^7$ and R$^8$, independently, is —C(O) (CH$_2$)$_m$CH$_3$ where m is an integer between 4–20, inclusive, —C(O)—(CH$_2$)$_7$CH═CH (CH$_2$)$_7$CH$_3$, —C(O)—(CH$_2$)$_7$CH═CH (CH$_2$)$_7$CH$_3$, —C(O)—CH$_2$)$_7$CH═CHCH$_2$CH═CH(CH$_2$)$_4$CH$_3$, or —C(O)—(CH$_2$)$_2$(CH$_2$CH═CH)$_4$(CH$_2$)$_4$CH$_3$, wherein each double bond, independently, is in a cis or trans configuration.

28. The compound of claim 17, wherein each of R$^6$, R$^{11}$, R$^{12}$, R$^{13}$, R$^{14}$, R$^{15}$, and R$^{16}$ is —CH$_2$OC(O)CH$_3$.

29. The compound of claim 17, wherein at least one of R$^2$, R$^3$, and R$^4$ are phosphorus-containing groups.

30. The compound of claim 17, wherein at least two of R$^2$, R$^3$, and R$^4$ are phosphorus-containing groups.

31. The compound of claim 17, wherein R$^2$, R$^3$, and R$^4$ are phosphorus-containing groups.

32. A pharmaceutical composition of the compound of claim 17.

33. The compound of claim 1 of the formula

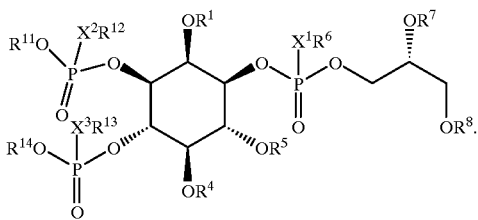

34. The compound of claim 33, wherein $R^4$ is —P(O)(OR$^{15}$)(X$^4$R$^{16}$).

35. The compound of claim 33, wherein each of $X^1$, $X^2$, $X^3$, and $X^4$ is O.

36. The compound of claim 33, wherein the caging group is 2-nitrobenzyl, 1-(2-nitrophenyl)ethyl, 4,5-dimethoxy-2-nitrobenzyl, 6nitropiperonyl, 4-hydroxyphenacyl, or 7-hydroxycoumarin-4-ylmethyl.

37. The compound of claim 33, wherein each of $R^7$ and $R^8$, independently, is —C(O) (CH$_2$)$_m$CH$_3$ where m is an integer between 4–20, inclusive, —C(O)—(CH$_2$)$_7$CH=CH (CH$_2$)$_7$CH$_3$, —C(O)—(CH$_2$)$_7$CH=CH(CH$_2$)$_7$CH$_3$, —C(O)—(CH$_2$)$_7$CH=CHCH$_2$CH=CH (CH$_2$)$_4$CH$_3$, or —C(O)—(CH$_2$)$_2$(CH$_2$CH$_2$CH=CH)$_4$(CH$_2$)$_4$CH$_3$, wherein each double bond, independently, is in a cis or trans configuration.

38. The compound of claim 33, wherein each of $R^6$, $R^{11}$, $R^{12}$, $R^{13}$, $R^{14}$, $R^{15}$, and $R^{16}$ is —CH$_2$OC(O)CH$_3$.

39. A pharmaceutical composition of the compound of claim 33.

* * * * *